US005451232A

United States Patent [19]
Rhinehart et al.

[11] Patent Number: 5,451,232
[45] Date of Patent: Sep. 19, 1995

[54] PROBE FOR MRI IMAGING AND SPECTROSCOPY PARTICULARLY IN THE CERVICAL REGION

[75] Inventors: Edward J. Rhinehart, Monroeville; Herbert Y. Kresel, Wynnesal; Mitchell Schnall, Lansdowne; Robert E. Lenkinski, Drexel Hill; Barton Milestone, Pittsburgh, all of Pa.

[73] Assignees: Medrad, Inc., Pittsburgh; The Trustees of the University of Pennsylvania, Philadelphia, both of Pa.

[21] Appl. No.: 132,152

[22] Filed: Oct. 5, 1993

Related U.S. Application Data

[63] Continuation of Ser. No. 771,419, Oct. 7, 1991, abandoned.

[51] Int. Cl.6 ............... A61B 5/055; A61M 25/10
[52] U.S. Cl. .................... 606/192; 606/197; 128/653.2; 128/653.5; 604/104; 604/96; 604/97
[58] Field of Search ............ 128/653.2, 653.5, 772, 128/778; 606/191-194, 197; 604/55, 96, 97, 104

[56] References Cited

U.S. PATENT DOCUMENTS

| 2,085,644 | 6/1937 | Ferciot ............... 128/407 |
| 2,126,257 | 8/1938 | Hird ............... 128/303.11 |
| 4,276,874 | 7/1981 | Wolvek et al. . |
| 4,338,942 | 4/1982 | Fogarty . |
| 4,349,033 | 9/1982 | Eden ............... 128/24 AA |
| 4,664,114 | 5/1987 | Ghodsian ............... 606/193 |
| 4,669,478 | 6/1987 | Robertson ............... 606/192 |
| 4,758,221 | 7/1988 | Jureidini . |
| 4,764,726 | 8/1988 | Misic et al. ............... 324/322 |
| 4,775,371 | 10/1988 | Mueller, Jr. . |
| 4,793,351 | 12/1988 | Landman et al. ............... 128/344 |
| 4,886,506 | 12/1989 | Lovgren et al. ............... 604/280 |
| 4,911,163 | 3/1990 | Fina ............... 606/127 |
| 4,920,318 | 4/1990 | Misic et al. ............... 324/318 |
| 4,960,106 | 10/1990 | Kubokawa et al. ............... 128/6 |
| 4,989,608 | 2/1991 | Ratner ............... 128/653 A |
| 5,035,231 | 7/1991 | Kubokawa et al. . |
| 5,050,607 | 9/1991 | Bradley et al. ............... 128/653 A |
| 5,071,406 | 12/1991 | Jang . |
| 5,104,377 | 4/1992 | Levine ............... 606/193 |
| 5,108,370 | 4/1992 | Walinsky ............... 606/194 |
| 5,116,305 | 5/1992 | Milder et al. . |
| 5,170,789 | 12/1992 | Narayan et al. . |

FOREIGN PATENT DOCUMENTS

| 0214721 | 3/1987 | European Pat. Off. . |
| 0249338 | 12/1987 | European Pat. Off. . |
| 0385367 | 9/1990 | European Pat. Off. ......... 128/653.5 |
| 61-90525 | 5/1986 | Japan . |
| 62-286451 | 12/1987 | Japan . |
| 63-49150 | 3/1988 | Japan . |
| 63-270036 | 11/1988 | Japan . |
| 64-20832 | 1/1989 | Japan . |
| 84/01513 | 4/1984 | WIPO . |
| 88/00071 | 1/1988 | WIPO . |

OTHER PUBLICATIONS

J. F. Schenck et al., "High Resolution Magnetic Resonance Imaging Using Surface Coils", Resonance Annual, pp. 123-160 (1986).

(List continued on next page.)

Primary Examiner—Krista M. Zele
Attorney, Agent, or Firm—Keck, Mahin & Cate

[57] ABSTRACT

An insertable intracavity probe for use in magnetic resonance imaging of an area of interest in a relatively inaccessible region of the body particularly the cervix is disclosed. The probe has an inflatable balloon structure with an internal pickup coil carried at the distal end of a shaft for rectal insertion of the coil and an inflatable anti-migration cuff to hold the probe in position and prevent outward migration thereof during a procedure. The balloon structure has an outer balloon shaped to facilitate insertion and accommodation of the coil to areas of the anatomy adjacent the cervix. Internally, the balloon structure has an inflatable balloon which can be used to adjust the shape of the coil to accommodate uniquely shaped anatomical areas.

9 Claims, 6 Drawing Sheets

OTHER PUBLICATIONS

Schnall et al., "The Development of an Intracavitary Inflatable Surface Coil for High Resolution Proton Imaging and Spectroscopy," Society of Magnetic Resonance in Medicine (Aug. 1986).

Martin et al., "Inflatable Surface Coil for MI Imaging of the Prostate", (Apr. 1988).

Otto et al., "High Resolution MR Imaging of the Prostate", Society of Magnetic Resonance Imaging, (Feb. 1987).

Narayan et al., "Transrectal Probe for H MRI and P MR Spectroscopy of the Prostate Gland", Magnetic Resonance in Medicine, Aug. 11, 1989, No. 2, pp. 209–220.

PROBE FOR MRI IMAGING AND SPECTROSCOPY PARTICULARLY IN THE CERVICAL REGION

This is a continuation of application Ser. No. 07/771,419, filed Oct. 7, 1991, now abandoned.

BACKGROUND OF THE INVENTION

This invention relates to a receiving device in the form of an intracavity probe for use in magnetic resonance imaging (MRI) and spectroscopy systems to enhance the imaging performance and spectroscopy sensitivity of such instruments when evaluating anatomical regions small in size relative to the body, and deep within the body, but proximate a location where an insertable pickup probe can be used. More particularly, the present invention relates to an intracavity pickup probe especially useful to image the cervical region by rectal introduction, but which may also be useful for inspecting other regions of the body by suitable intracavity insertion.

In the field of MRI systems, also commonly known as NMR imaging systems, external pickup probes are typically used for receiving radio frequency signals from the anatomical region of interest. For optimum performance when imaging certain select parts of the body, the pickup probe should be insertable for intracavity use and include a radio frequency receiving coil, to be positioned as close to the region of interest as possible. In addition, the insertable pickup probe should also have a sensitive volume equaling the desired field of view of the region of interest. This allows optimization of the "filling factor" and "coupling coefficient" for the specific MRI system, thereby improving signal-to-noise ratio in MR imaging.

Furthermore, for optimum sensitivity, the receiving coil should have an unloaded coil quality factor (Q) which is as great as possible and should be adjusted to resonate at the exact Larmour frequency of the scanner of the MRI system. It also sometimes is desired that the insertable, intracavity pickup probe be disposable, and hence the cost of the probe should be minimized as much as possible. At the same time, it is important that in reducing the cost of the probe, the ability to impedance match and tune the receiving coil to the scanner of the MRI system not be compromised. Therefore, there is a need to provide a disposable pickup probe at minimal cost for use in a MRI system which is capable of automatic or manual tuning and impedance matching the receiving coil to the scanner of the MRI system.

SUMMARY OF THE INVENTION

It is an object of the present invention to provide an insertable, intracavity pickup probe capable of being placed in close proximity to a region of interest particularly the cervix to improve the quality of a magnetic resonance image or spectrum.

It is a further object of the present invention to provide an insertable MRI pickup probe capable of being accurately positioned relative to an area of interest which is in a relatively inaccessible region of the body such as the cervix.

Another object of the invention is to provide an insertable MRI pickup probe which when inserted adjacent a site of interest in a body cavity can be manipulated so as to optimize the size and/or shape of the pickup coil in relation to the particular area of interest.

Another object of the invention is to provide an insertable MRI pickup probe which includes an anti-migration device on a shaft of the probe which can be inflated when inserted in a body cavity to prevent the probe from working its way out of the cavity.

A still further object of the invention is to provide an insertable MRI pickup probe having an outer shape which facilitates manipulation of the probe into body cavities and placement of the pickup coil adjacent an area of interest particularly one in the cervical region. In this regard, a more specific object of the invention is to provide a probe having an outer shape which facilitates rectal insertion of the probe and positioning thereof adjacent the cervix in a manner allowing optimal positioning and shaping of the pickup coil to accommodate portions of the female anatomy adjacent an area of interest in the cervix.

The invention in a specific embodiment relates to an insertable, intracavity pickup probe, and more specifically an intrarectal pickup probe for high sensitivity and high resolution imaging of the cervix and associated area. Although the pickup probe is described hereinafter as principally to image or obtain spectra from the area of the cervix, it should be understood that the concepts outlined herein are equally appropriate for other regions of interest such as the rectum, vagina, bladder and mouth. Additionally, the principles described herein may be applied to MRI or NMR application involving the arteries, veins, and other similar regions of the body reachable by an insertable or implantable pickup probe.

The insertable pickup probe of the present invention greatly improves the signal-to-noise ratio of an image or spectrum acquisition over signal pickup devices commonly used with MRI and NMR scanner systems. In addition, the restricted field of view of the probe reduces or eliminates image distortion caused by motion, blood flow, patient breathing, and signal aliasing when conducting an image acquisition using multidimensional fast Fourier transform techniques.

The insertable pickup probe of the present invention comprises a shaft which supports a patient interface which comprises an expansible RF receiving structure balloon at its distal end. In a specific embodiment, the interface balloon structure contains a receiving coil in the form of a closed substantially planar loop with opposite sides of the loop extending longitudinally relative to the shaft. An internal balloon assembly is positioned within the structure, having inflatable arms each extending outwardly from the shaft and along one of the respective lengthwise sides of the coil, which is suitably attached, as by adhesive strips or the like to the respective balloons. The inflatable arms have a common or separate inflation tubes which extend through the shaft, exiting at the proximal handle end thereof. Each tube has a stopcock or like inflation controller, and is connectable to an inflation device. The coil is provided with an electrical lead which also extends through the shaft, exiting at the proximal handle end and being provided with a connector for attaching the coil to an interface network to receive signals from the coil.

The effect of inflating the balloon arms is to expand the coil outwardly from the shaft, effectively increasing the overall width and area of the coil. Conversely, the effect of deflating the balloon arms is to laterally contract the coil, decreasing its width and area. Accordingly, the size and shape of the coil can be adjusted dependent on the degree of inflation of the balloons.

The balloon may be substantially horseshoe shaped with the respective arms each having terminal ends. Preferably however, the balloon may be in the form of a continuous ring with the arms forming opposite sides of the ring.

When the probe is inserted in a body cavity with the balloon structure positioned adjacent an area of interest to be investigated by NMR or MRI imaging, the provision of the inflatable internal arms allows the coil to be more effectively shaped and fitted relative to the area of interest by selective inflation of the arms.

In accordance with another aspect of the invention, the probe may include an outer balloon in which the coil and inner balloon assembly is accommodated, which facilitates rectal insertion and positioning in a location adjacent the cervix and which is particularly shaped and configured so as to conform to required portions of the anatomy when investigating areas of the cervix. To this end, the outer balloon in accordance with the invention may have an elongate slightly curved form with inner and outer concave and convex surfaces respectively, the outer convex surface being formed with a lengthwise depression or channel.

To provide an indication of the orientation of the coil, the shaft may include a longitudinal sight line or stripe aligned with the coil. Also the shaft may be relatively flexible and provided with a removable stiffener tube or mandrel.

According to yet another aspect of the invention, the shaft of the probe may be provided with an inflatable annular anti-migration cuff to prevent the probe working out of a body cavity when inserted. The cuff may be fixed in relation to the shaft and inflated through the same tube (or shaft lumen) which inflates the inner balloon. In this case, the material of the cuff is such as to provide preferential inflation of the balloon such that in use, the balloon and cuff inflate in sequence. In another embodiment, the inflatable cuff may be slidable along the shaft on a sleeve (only when uninflated) and have an inflation tube separate from that of the inner balloon. The movable anti-migration cuff allows the depth of insertion of the probe to be varied to suit different size anatomies.

The above and other objects and advantages of the present invention will become more readily apparent when reference is made to the following description, taken in conjunction with the accompanying drawings.

DESCRIPTION OF PREFERRED EMBODIMENTS

Figure 1:
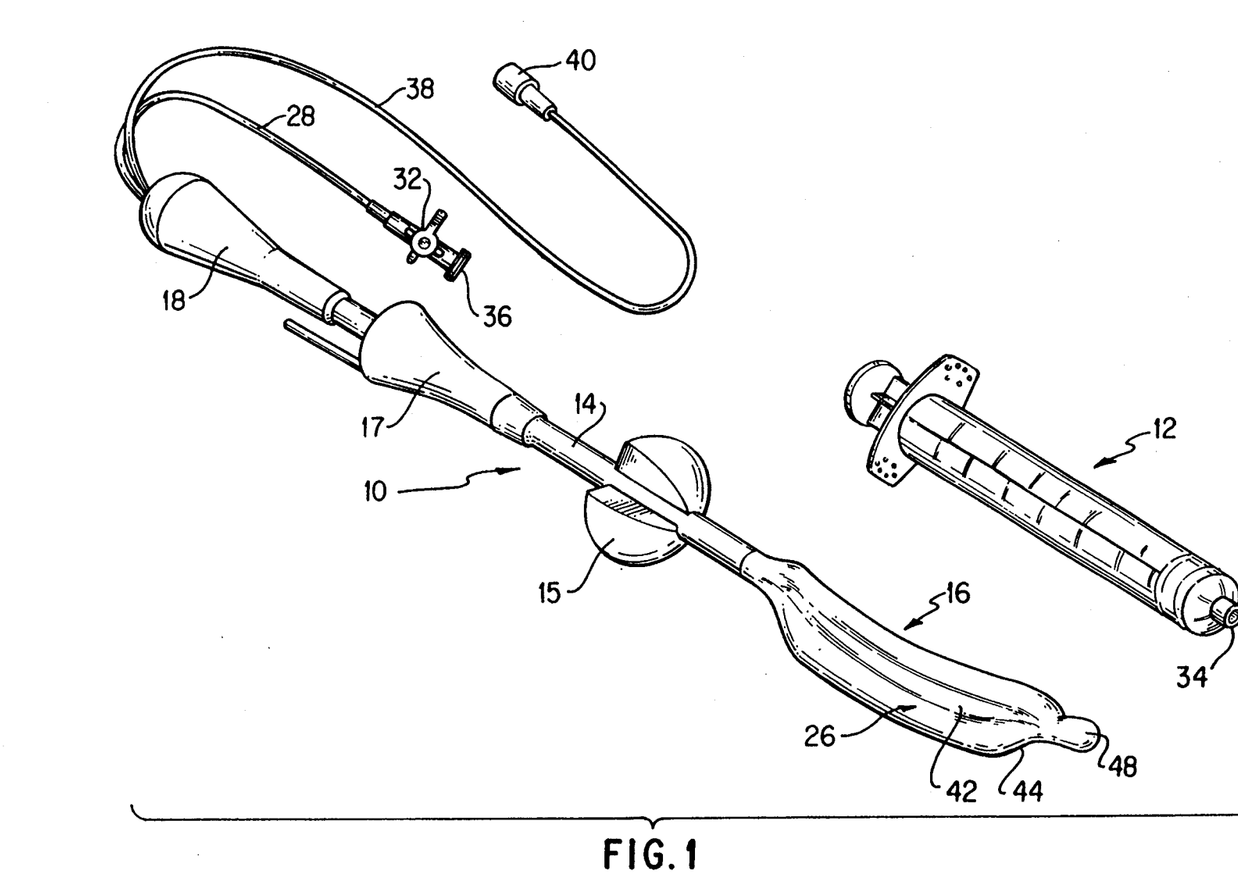
FIG. 1 is a perspective view of an insertable pickup probe in accordance with the present invention and an associated inflation pump.

Referring first to FIG. 1, an insertable cervical pickup probe is shown in an assembled form at 10, and an inflation pump to which the probe connects is shown at 12. The pickup probe 10 is an MRI or NMR receiving device capable of imaging or gathering spectra from the human cervix and surrounding tissue, but may also be used as the transmit coil for RF excitation. The probe 10 is used with an interface network (not shown) which provides the tuning, impedance matching, and decoupling functions in known manner.

The probe 10 includes a shaft 14 which supports a patient interface expansible RF receiving bladder-like membrane or balloon structure 16 at its distal end, an anti-migration disc 15, an introducer 17 and a handle 18 located at the proximal end of the shaft 14. (The anti-migration disc may be replaced or supplemented by an inflatable anti-migration cuff, still to be described.) As will be described in more detail later, assembly 16 includes an internal pickup coil 20 and a second expansible bladder-like membrane, such as the internal inflatable balloon 22 shown in FIG. 2. The coil and internal balloon structure are accommodated, as will be described, in a first expansible membrane, shown as an outer balloon 26. As is evident from the figures, both the first and second membranes are configured to be expanded only in generally opposed directions that are confined within a single plane so that the relative thickness or height of assembly 16 never increases significantly, even though the width does. A tube 28, for inflating the internal balloon structure extends through shaft 14 and exits at the proximal end of handle 18. The tube has an inflation control stopcock 32, and a connection 36, for attaching same to the nozzle 34 of pump 12.

The receiving coil contained within the patient interface balloon structure 16 can be electrically connected to an interface network by an insulated interconnecting cable 38 which has a plug 40 at its proximal end.

Figures 3, 4:
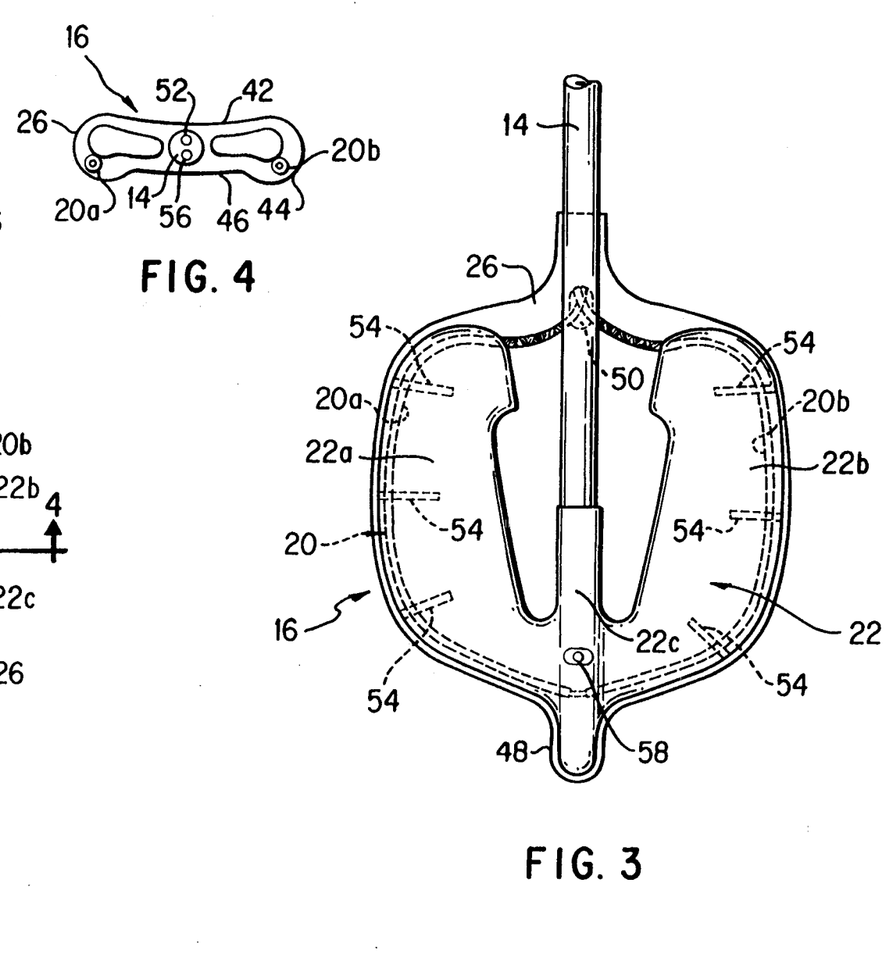
FIG. 3 is a cross-sectional plan view of the distal end balloon portion illustrated in an inflated condition.
FIG. 4 is a sectional view taken on line 4—4 of FIG. 2.
Figure 5:
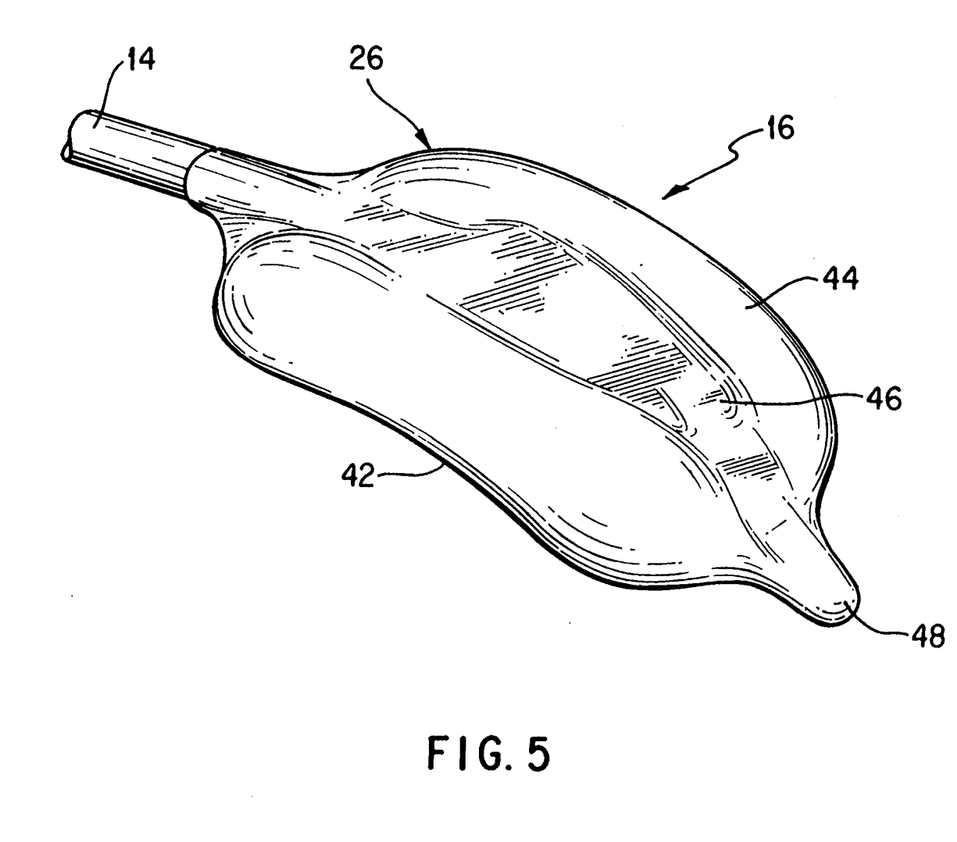
FIG. 5 is a perspective view of the distal balloon portion of the probe.

The outer balloon 26 of the balloon structure 16, in order to facilitate rectal insertion and accommodation to portions of the female anatomy adjacent the cervix is of a generally elongate form and has a slight lengthwise curvature with an inner concave surface 42 and an outer convex surface 44. The outer convex surface 44 has a lengthwise depression or channel 46 as best seen in FIGS. 4 and 5. The outer balloon is formed of suitable elastic material and has a distal end nipple 48 accommodating the tip of shaft 14. The tip end portion of the shaft may be somewhat more flexible than the shaft itself.

Coil 20 is of a generally planar rectangular form accommodated inside balloon 26 adjacent the shaft 14. The respective coil leads extend through an aperture 50 in the shaft and internally of the shaft the leads extend into cable 38 which passes through a cable lumen 52 formed in the shaft (see FIG. 4). The coil 20 has opposite lengthwise side portions 20a and 20b.

Internal balloon 22 is generally horseshoe-shaped, having a central sock or cuff portion 22c received on the distal end portion of shaft 14, and opposing arm portions 22a, 22b which extend outwardly from the sock portion and along the respective side portions 20a, 20b of the coil. The respective arm portions 22a, 22b of the balloon may be secured to the respective side portions 20a, 20b of the coil by adhesive gauze strips 54 or the like. The balloon is preferably made of non-stretchable flexible material and thereby permits lateral expansion while limiting any increase in thickness, due to the preselected shape of the membrane. For inflating balloon 22, shaft 14 has an airline lumen 56 (FIG. 4) connected to tube 28 and terminating in an aperture 58 opening into the balloon.

Figure 2:
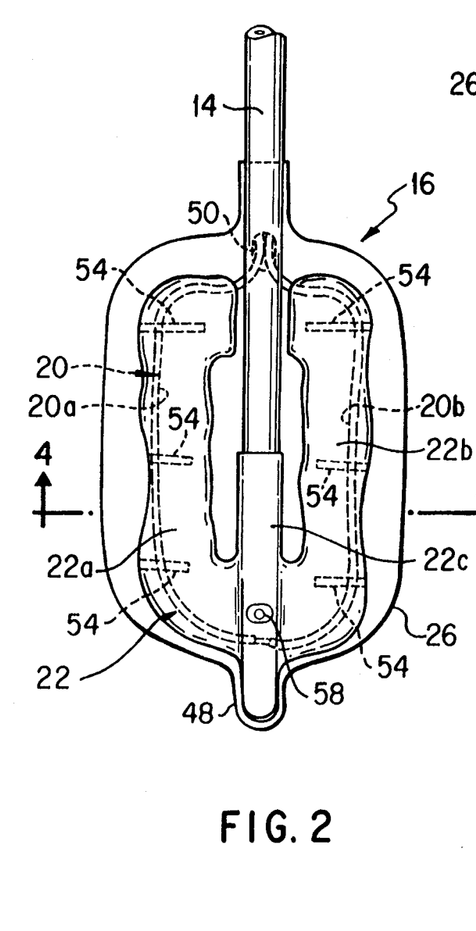
FIG. 2 is a cross-sectional plan view of the distal balloon portion of the insertable pickup probe illustrated in a deflated condition.

With balloon 22 deflated, as shown in FIG. 2, the coil 20 has a narrow, reduced area configuration. This condition is suitable for inserting the probe through the rectum to position same adjacent a cervical area to be investigated. Inflation of balloon 22 by means of pump 12 causes the arms 22a and 22b to expand outwardly (FIG. 3) with corresponding lateral expansion of coil 20 and an increase of the coil area. It will be evident that the coil can thus be effectively shaped in a controlled manner upon insertion of the probe by inflating the arms of balloon 22 to selected inflation pressures in order to accommodate the coil to uniquely shaped areas of the anatomy.

Figure 6:
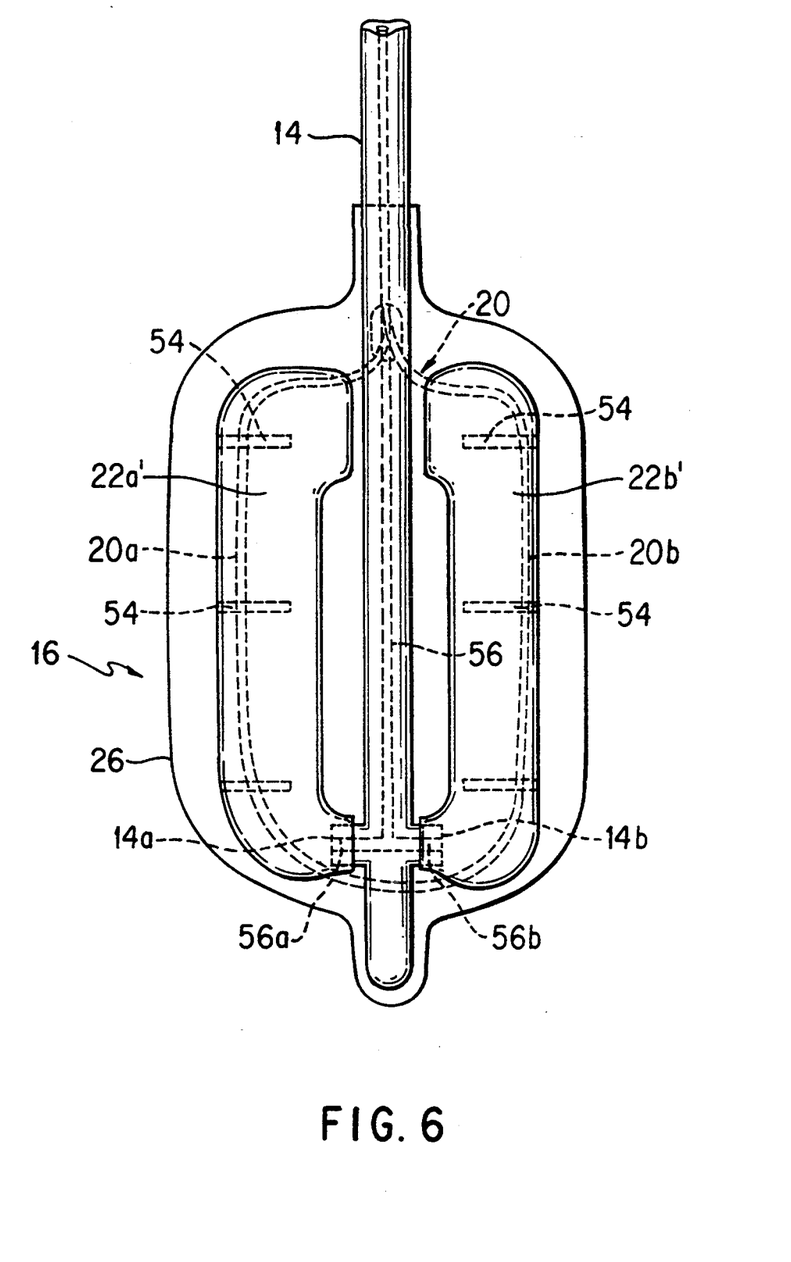
FIG. 6 is a view similar to FIG. 2 of a second embodiment pickup probe.

An alternative arrangement for the balloon structure 16 is shown in FIG. 6, where like references are used to denote parts which are equivalent to those in the previous figures. In the alternative arrangement, the shaft 14 has diametrically opposed extensions 14a and 14b at its distal end, and the internal balloon 22 is effectively divided into two separate balloon arms 22a' and 22b' which fit on the respective extensions and extend along the opposite sides 20a and 20b of coil 20 as in the previous arrangement. In the FIG. 6 embodiment, airline lumen 56 divides into branches 56a, 56b for simultaneously inflating the respective balloon arms 22a', 22b'. Otherwise, functioning of the probe is substantially identical to the previously described probe.

In a further, non-illustrated embodiment similar to that shown in FIG. 6, the respective balloon arms may be separately and independently inflated by means of separate airline lumens extending through the shaft.

Figure 7:
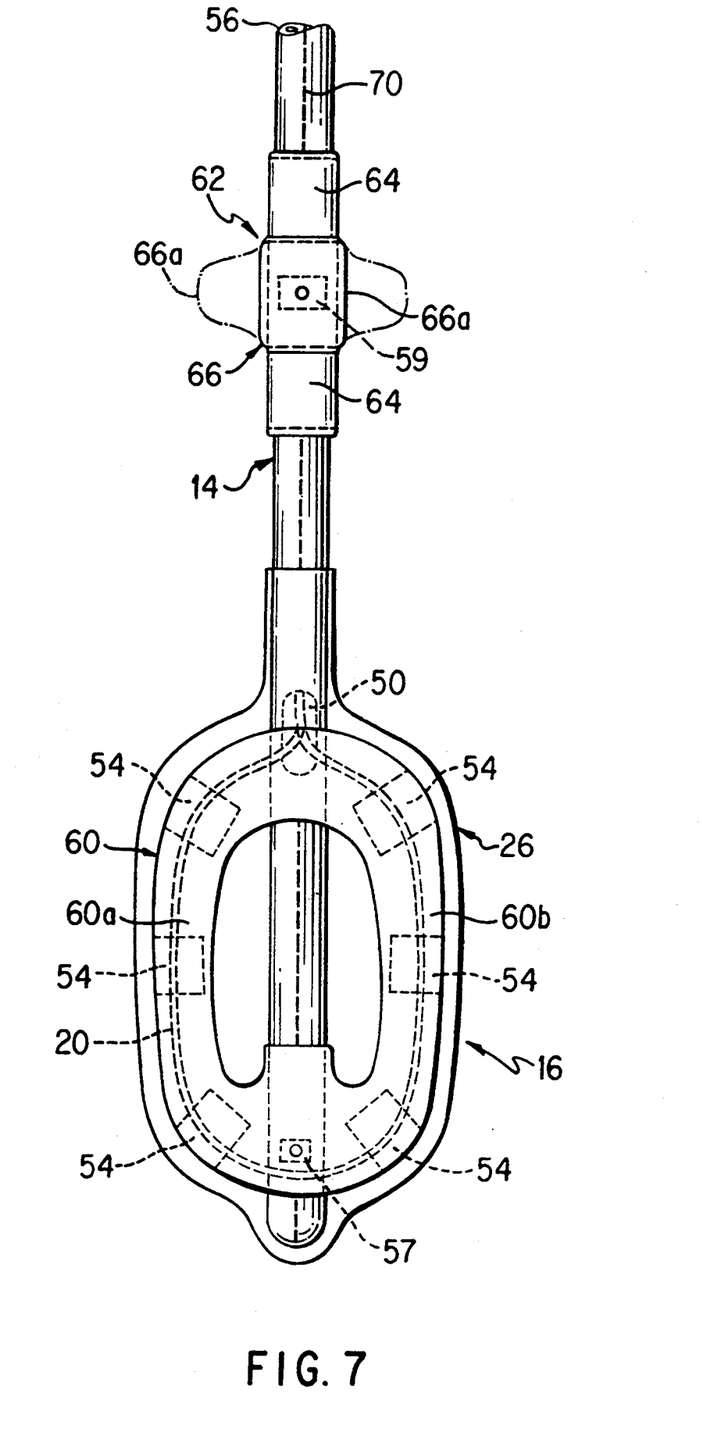
FIG. 7 is a view similar to FIGS. 2 and 6 of a third embodiment pickup probe, incorporating an anti-migration cuff.

FIG. 7 shows a preferred balloon arrangement in which the internal balloon 60 is of a continuous ring-like form with opposite arms 60a and 60b again taped to opposite side portions the coil 20 by adhesive strips 54. As previously, the balloon may be inflated through air line lumen 56 formed in the shaft 14 with an outlet 57 communicating with the balloon. The balloon may be secured to the shaft by a cuff as in the previous embodiment or may be adhesively secured on one side of the shaft with an inlet aperture (not shown) communicating with outlet 57. As in the previous embodiments, inflation of balloon 60 is effective to expand the opposite sides of the coil outwardly and deflation of the balloon contracts the coil.

The embodiment shown in FIG. 7 also illustrates another feature of the invention although this feature is not limited in its application to the FIG. 7 embodiment. Thus, there is provided on shaft 14 an inflatable anti-migration cuff 62 comprising a sleeve 66 of inflatable elastic material, secured in sealed manner over the shaft by sealing sleeves 64 while leaving a central section 66a of sleeve 66 uncovered. The central section 66a is disposed over a second outlet 59 of the airline lumen 56 so that air pressure applied through lumen 56 can expand the central section 66a from its normally flattened state (solid line) into an expanded or distended balloon-like doughnut (dotted line) around the shaft. Thus, when the probe is inserted in a body cavity, inflation of sleeve 66 is useful to prevent outward migration of the probe from the body cavity. Further, the materials of balloon 60 and sleeve 66 preferably are chosen to promote preferential inflation of the balloon 60, so that when inserted in a body cavity balloon 60 will inflate prior to sleeve 66. Alternatively sleeve 66 could be provided with inflation means independent of airline lumen 56.

FIG. 7 also illustrates another feature of the invention, equally useful in the other embodiments, namely a stripe 70 along the shaft (shown dotted for clarity) to indicate the orientation of coil 20 when the probe is inserted. The stripe, or other equivalent marking, should be at least at the proximal end of the shaft.

Figure 8:
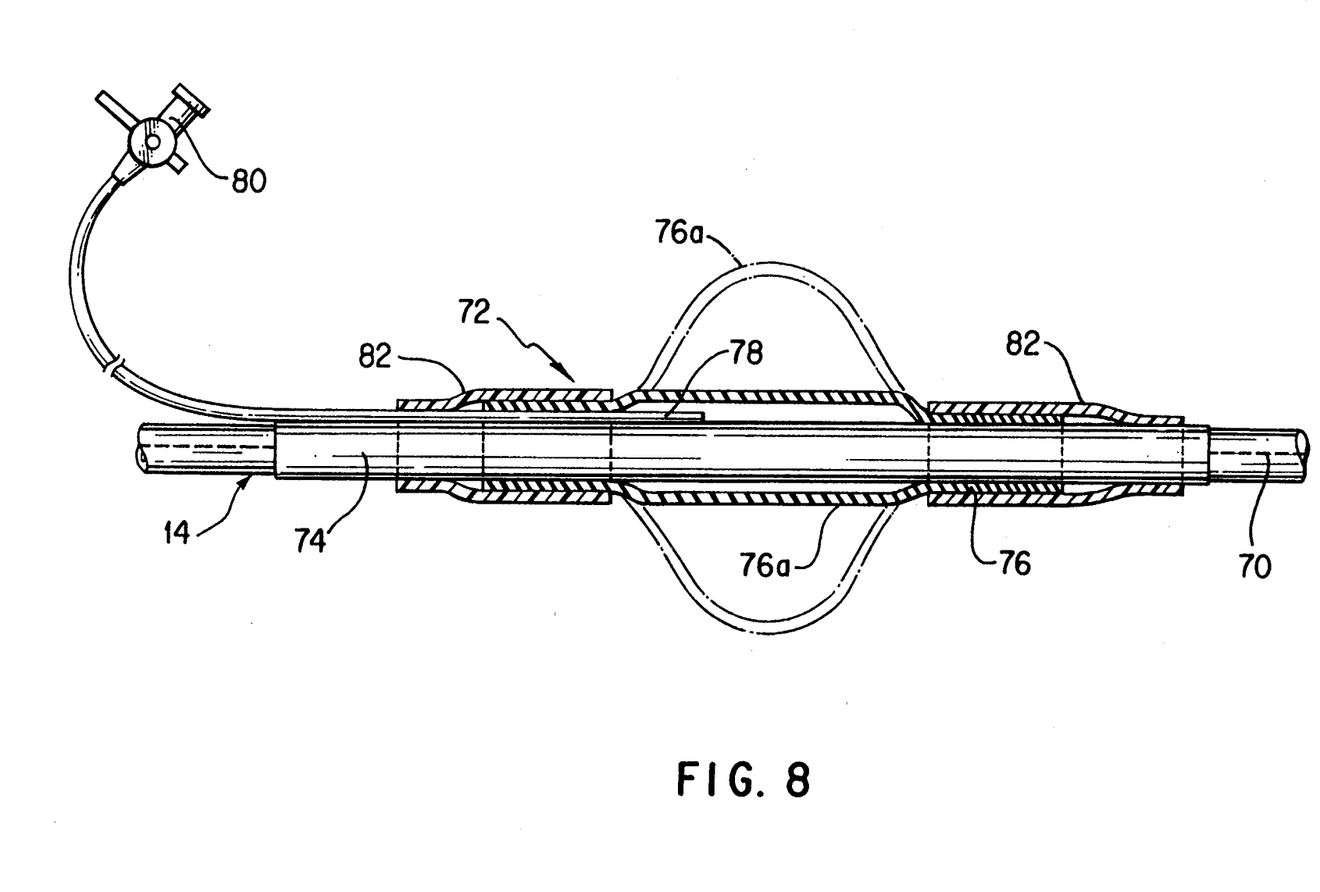
FIG. 8 is a longitudinal sectional view of another form of anti-migration cuff on the shaft of a pickup probe.

FIG. 8 shows an alternative form of inflatable anti-migration cuff 72 which can be selectively adjusted along the shaft 14 on a sliding sleeve 74. In this case, an inflatable sleeve 76 is fitted over sleeve 74 and its opposite end portions are sealed to sleeve 74 by sealing sleeves 82. A central portion 76a of sleeve 76 is again left uncovered and an inflation tube 78 extends through the seal at one end of the structure into the interior of central portion 76a. Tube 78 is provided with a stopcock 80 which can be connected to an inflation pump. Again, when the probe is inserted in a body cavity, central portion 76a of the sleeve can be inflated from its normal flat state (full line) into a distended balloon like doughnut (dotted line) to prevent outward migration of the probe. In this embodiment, the anti-migration cuff can be adjusted lengthwise of shaft 14 (only when uninflated) to adjust the depth of penetration of the probe to suit different size anatomies.

While only preferred embodiments of the invention have been described herein in detail, the invention is not limited thereby, and modifications can be made within the scope of the attached claims.

We claim:

1. An insertable intracavity probe for use in magnetic resonance imaging of a region of interest within a cavity of a patient, said probe comprising:
   an elongate shaft having proximate and distal ends; and
   an expansible RF receiving structure on the distal end of the shaft, the expansible structure having height and width dimensions both perpendicular to the shaft axis and comprising:
   (a) an external expansible membrane mounted on the shaft;
   (b) an expansion means mounted on the distal end of the shaft within the volume enclosed by the external membrane, the expansion means causing expansion of the external membrane in opposed directions perpendicular to the shaft and substantially confined within a single plane defined by the width dimension; and
   inflation means for inflating the expansible RF structure into an expanded state; and wherein the width dimension of the expansible structure is substantially greater than the height dimension in the expanded state.

2. A probe as defined in claim 1 wherein the expansion means comprises a second expansible membrane constructed of a non-stretchable flexible material.

3. A probe as defined in claim 1 wherein the external expansible membrane is constructed of an elastic material.

4. A probe as defined in claim 1 wherein the expansion means is configured as two closed loops.

5. A probe as defined in claim 1 wherein the expansion means is configured to form longitudinal arm portions.

6. An insertable intracavity probe for use in magnetic resonance imaging of a region of interest within a cavity of a patient comprising an elongate shaft having a proximal end, a distal end, a handle on the proximal end of the shaft, and a balloon structure on the distal end of the shaft, the balloon structure including an outer balloon, a pickup coil in the outer balloon, the coil having an electrical lead for connecting the coil to an interface network, inflatable internal balloon means connected to the coil within the outer balloon for selectively adjusting the shape of the coil by inflation and deflation of the balloon means, and inflation means for inflating and deflating the balloon means, wherein the balloon means comprises opposed balloon arms each extending along opposed side portions of the coil respectively for expanding the coil laterally by inflation of the balloon arms and contracting the coil laterally by deflation of the balloon arms, and wherein the shaft has opposed lateral extensions on which the respective balloon arms are mounted through openings in the respective arms, and the inflation means includes airline lumen branches in the respective extensions.

7. A probe as defined in claim 6 wherein the airline lumen branches extend outwardly from a common airline lumen formed through the shaft.

8. An insertable intracavity probe for use in magnetic resonance imaging of a region of interest within a cavity of a patient comprising an elongate shaft having a proximal end, a distal end, a handle on the proximal end of the shaft, and a balloon structure on the distal end of the shaft, the balloon structure including an outer balloon, a pickup coil in the outer balloon, the coil having an electrical lead for connecting the coil to an interface network, inflatable internal balloon means connected to the coil within the outer balloon for selectively adjusting the shape of the coil by inflation and deflation of the balloon means, and inflation means for inflating and deflating the balloon means, wherein the balloon means comprises opposed balloon arms each extending along opposed side portions of the coil respectively for expanding the coil laterally by inflation of the balloon arms and contracting the coil laterally by deflation of the balloon arms, and wherein the balloon arms are connected to the respective side portions of the coil by adhesive means.

9. An insertable intracavity probe for use in magnetic resonance imaging of a region of interest within a cavity of a patient comprising an elongate shaft having a proximal end, a distal end, a handle on the proximal end of the shaft, and a balloon structure on the distal end of the shaft, the balloon structure including an outer balloon, a pickup coil in the outer balloon, the coil having an electrical lead for connecting the coil to an interface network, inflatable internal balloon means connected to the coil within the outer balloon for selectively adjusting the shape of the coil by inflation and deflation of the balloon means, and inflation means for inflating and deflating the balloon means, wherein the balloon means comprises opposed balloon arms each extending along opposed side portions of the coil respectively for expanding the coil laterally by inflation of the balloon arms and contracting the coil laterally by deflation of the balloon arms, and wherein the balloon means is of a horseshoe-like shape.

* * * * *